US009354156B2

(12) United States Patent
Lee et al.

(10) Patent No.: US 9,354,156 B2
(45) Date of Patent: May 31, 2016

(54) MICROFLUIDIC PARTICLE ANALYSIS METHOD, DEVICE AND SYSTEM

(75) Inventors: Philip Janmin Lee, Alameda, CA (US); Paul Ju-Sung Hung, Fremont, CA (US); Narendra Maheshri, Cambridge, MA (US)

(73) Assignee: EMD Millipore Corporation, Billerica, MA (US)

( * ) Notice: Subject to any disclaimer, the term of this patent is extended or adjusted under 35 U.S.C. 154(b) by 125 days.

(21) Appl. No.: 12/019,857

(22) Filed: Jan. 25, 2008

(65) Prior Publication Data

US 2008/0194012 A1 Aug. 14, 2008

Related U.S. Application Data

(60) Provisional application No. 60/900,651, filed on Feb. 8, 2007.

(51) Int. Cl.
*C12M 1/34* (2006.01)
*G01N 15/14* (2006.01)
*B01L 3/00* (2006.01)

(52) U.S. Cl.
CPC ...... *G01N 15/1484* (2013.01); *B01L 3/502761* (2013.01); *B01L 3/502707* (2013.01); *B01L 2200/0668* (2013.01); *B01L 2300/0867* (2013.01); *B01L 2400/0481* (2013.01); *B01L 2400/0487* (2013.01); *B01L 2400/0655* (2013.01); *G01N 15/147* (2013.01); *G01N 15/1475* (2013.01); *G01N 2015/1493* (2013.01)

(58) Field of Classification Search
CPC ............ B01L 3/502761; B01L 3/502707; B01L 2200/0668; B01L 2300/0867; B01L 2400/0481; B01L 2400/0655; B01L 2400/0487; G01N 5/1484; G01N 5/147; G01N 5/1475; G01N 2015/1493
USPC ................................ 435/288.5, 305.2
See application file for complete search history.

(56) References Cited

U.S. PATENT DOCUMENTS

| 4,055,613 | A | 10/1977 | Kapral |
| 4,661,455 | A | 4/1987 | Hubbard |
| 4,734,373 | A | 3/1988 | Bartal |
| 4,748,124 | A | 5/1988 | Vogler |
| 5,079,168 | A | 1/1992 | Amiot |
| 5,153,131 | A | 10/1992 | Wolf et al. |

(Continued)

FOREIGN PATENT DOCUMENTS

| DE | 19948087 A1 | 5/2001 |
| EP | 0155237 A2 | 9/1985 |

(Continued)

OTHER PUBLICATIONS

Chang et al. (2006) "Fabrication of polymer microlens arrays using capillary forming with a soft mold of microholes array and UV-curable polymer." Optical Society of America 14(13): 6253-6258.

(Continued)

*Primary Examiner* — Michael Hobbs
(74) *Attorney, Agent, or Firm* — Nields, Lemack & Frame, LLC

(57) ABSTRACT

The method, device, and system relate to particle analysis, and in particular, to a microfluidic device designed for trapping particles for analysis. Particles include beads and cells.

20 Claims, 14 Drawing Sheets

(56) References Cited

U.S. PATENT DOCUMENTS

| | | |
|---|---|---|
| 5,310,676 A | 5/1994 | Johansson et al. |
| 5,330,908 A | 7/1994 | Spaulding |
| 5,376,252 A | 12/1994 | Ekstrom et al. |
| 5,416,022 A | 5/1995 | Amiot |
| 5,424,209 A | 6/1995 | Kearney |
| 5,437,998 A | 8/1995 | Schwarz et al. |
| 5,451,524 A | 9/1995 | Coble et al. |
| 5,462,874 A | 10/1995 | Wolf et al. |
| 5,565,353 A | 10/1996 | Klebe et al. |
| 5,589,112 A | 12/1996 | Spaulding |
| 5,593,814 A | 1/1997 | Matsuda et al. |
| 5,602,028 A | 2/1997 | Minchinton |
| 5,627,070 A | 5/1997 | Gruenberg |
| 5,637,469 A | 6/1997 | Wilding et al. |
| 5,641,644 A | 6/1997 | Klebe |
| 5,658,797 A | 8/1997 | Bader |
| 5,686,301 A | 11/1997 | Falkenberg et al. |
| 5,686,304 A | 11/1997 | Codner |
| 5,693,537 A | 12/1997 | Wilson et al. |
| 5,702,941 A | 12/1997 | Schwarz |
| 5,714,384 A | 2/1998 | Wilson et al. |
| 5,763,261 A | 6/1998 | Gruenberg |
| 5,763,275 A | 6/1998 | Nagels et al. |
| 5,763,279 A | 6/1998 | Schwarz et al. |
| 5,786,215 A | 7/1998 | Brown et al. |
| 5,793,440 A | 8/1998 | Nakasaka et al. |
| 5,801,054 A | 9/1998 | Kiel et al. |
| 5,866,345 A | 2/1999 | Wilding et al. |
| 5,882,918 A | 3/1999 | Goffe |
| 5,900,361 A | 5/1999 | Klebe |
| 5,912,177 A | 6/1999 | Turner et al. |
| 5,924,583 A | 7/1999 | Stevens et al. |
| 5,932,315 A | 8/1999 | Lum et al. |
| 5,942,443 A | 8/1999 | Parce et al. |
| 6,039,897 A | 3/2000 | Lochhead et al. |
| 6,048,498 A | 4/2000 | Kennedy |
| 6,096,532 A | 8/2000 | Armstrong et al. |
| 6,107,085 A | 8/2000 | Coughlin et al. |
| 6,153,073 A | 11/2000 | Dubrow et al. |
| 6,190,913 B1 | 2/2001 | Singh |
| 6,197,575 B1 | 3/2001 | Griffith et al. |
| 6,228,635 B1 | 5/2001 | Armstrong et al. |
| 6,238,908 B1 | 5/2001 | Armstrong et al. |
| 6,251,343 B1 | 6/2001 | Dubrow et al. |
| 6,274,337 B1 | 8/2001 | Parce et al. |
| 6,277,642 B1 | 8/2001 | Mentzen et al. |
| 6,297,046 B1 | 10/2001 | Smith et al. |
| 6,323,022 B1 | 11/2001 | Chang et al. |
| 6,326,211 B1 | 12/2001 | Anderson et al. |
| 6,403,369 B1 | 6/2002 | Wood |
| 6,410,309 B1 | 6/2002 | Barbera-Guillem et al. |
| 6,455,310 B1 | 9/2002 | Barbera-Guillem |
| 6,465,243 B2 | 10/2002 | Okada et al. |
| 6,468,792 B1 | 10/2002 | Bader |
| 6,481,648 B1 | 11/2002 | Zimmermann |
| 6,495,104 B1 | 12/2002 | Unno et al. |
| 6,518,035 B1 | 2/2003 | Ashby et al. |
| 6,534,013 B1 | 3/2003 | Kennedy |
| 6,548,263 B1 | 4/2003 | Kapur et al. |
| 6,551,841 B1 | 4/2003 | Wilding et al. |
| 6,555,365 B2 | 4/2003 | Barbera-Guillem et al. |
| 6,562,616 B1 | 5/2003 | Toner et al. |
| 6,569,675 B2 | 5/2003 | Wall et al. |
| 6,576,458 B1 | 6/2003 | Sarem et al. |
| 6,585,744 B1 | 7/2003 | Griffith |
| 6,585,939 B1 | 7/2003 | Dapprich |
| 6,593,136 B1 | 7/2003 | Geiss |
| 6,637,463 B1 | 10/2003 | Lei et al. |
| 6,648,015 B1 | 11/2003 | Chow |
| 6,653,124 B1 | 11/2003 | Freeman |
| 6,673,595 B2 | 1/2004 | Barbera-Guillem |
| 6,756,019 B1 | 6/2004 | Dubrow et al. |
| 6,759,245 B1 | 7/2004 | Toner et al. |
| 6,794,184 B1 | 9/2004 | Mohr et al. |
| 6,811,752 B2 | 11/2004 | Barbera-Guillem |
| 6,821,772 B2 | 11/2004 | Barbera-Guillem et al. |
| 6,846,668 B1 * | 1/2005 | Garman et al. ............ 435/285.1 |
| 6,857,449 B1 | 2/2005 | Chow |
| 6,908,767 B2 | 6/2005 | Bader |
| 6,915,679 B2 | 7/2005 | Chien et al. |
| 6,969,166 B2 | 11/2005 | Clark et al. |
| 7,005,292 B2 | 2/2006 | Wilding et al. |
| 7,018,830 B2 | 3/2006 | Wilding et al. |
| 7,022,518 B1 | 4/2006 | Feye |
| 7,067,263 B2 | 6/2006 | Parce et al. |
| 7,141,386 B2 | 11/2006 | Dunfield et al. |
| 7,155,344 B1 | 12/2006 | Parce et al. |
| 7,160,687 B1 | 1/2007 | Kapur et al. |
| 7,171,983 B2 | 2/2007 | Chien et al. |
| 7,192,769 B2 | 3/2007 | Pykett et al. |
| 7,223,371 B2 | 5/2007 | Hayenga et al. |
| 7,343,248 B2 | 3/2008 | Parce et al. |
| 7,745,209 B2 | 6/2010 | Martin et al. |
| 7,919,319 B2 | 4/2011 | Jervis et al. |
| 8,257,964 B2 | 9/2012 | Hung et al. |
| 8,673,625 B2 | 3/2014 | Hung et al. |
| 8,709,790 B2 | 4/2014 | Hung et al. |
| 9,206,384 B2 | 12/2015 | Lee et al. |
| 2002/0039785 A1 | 4/2002 | Schroeder et al. |
| 2002/0108860 A1 | 8/2002 | Staats |
| 2002/0110905 A1 | 8/2002 | Barbera-Guillem et al. |
| 2002/0177221 A1 | 11/2002 | Nishiguchi et al. |
| 2003/0008388 A1 | 1/2003 | Barbera-Guillem et al. |
| 2003/0008389 A1 | 1/2003 | Carll |
| 2003/0030184 A1 | 2/2003 | Kim |
| 2003/0040104 A1 | 2/2003 | Barbera-Guillem |
| 2003/0124623 A1 | 7/2003 | Yager et al. |
| 2003/0143727 A1 | 7/2003 | Chang |
| 2003/0156992 A1 | 8/2003 | Anderson et al. |
| 2003/0211012 A1 | 11/2003 | Bergstrom |
| 2004/0029266 A1 | 2/2004 | Barbera-Guillem |
| 2004/0043481 A1 | 3/2004 | Wilson |
| 2004/0072278 A1 | 4/2004 | Chou et al. |
| 2004/0096960 A1 * | 5/2004 | Burd Mehta et al. ...... 435/287.2 |
| 2004/0132175 A1 | 7/2004 | Vetillard et al. |
| 2004/0202579 A1 | 10/2004 | Larsson |
| 2004/0229349 A1 | 11/2004 | Daridon |
| 2004/0238484 A1 | 12/2004 | Le Pioufle et al. |
| 2005/0009179 A1 | 1/2005 | Gemmiti et al. |
| 2005/0019213 A1 | 1/2005 | Kechagia et al. |
| 2005/0032208 A1 | 2/2005 | Oh et al. |
| 2005/0072946 A1 * | 4/2005 | Studer et al. ................... 251/11 |
| 2005/0101009 A1 | 5/2005 | Wilson et al. |
| 2005/0106717 A1 | 5/2005 | Wilson et al. |
| 2005/0169962 A1 | 8/2005 | Bhatia et al. |
| 2005/0214173 A1 | 9/2005 | Facer et al. |
| 2005/0221373 A1 * | 10/2005 | Enzelberger et al. ............. 435/6 |
| 2005/0260063 A1 | 11/2005 | Domansky et al. |
| 2005/0266582 A1 | 12/2005 | Modlin et al. |
| 2006/0003436 A1 | 1/2006 | DiMilla et al. |
| 2006/0031955 A1 | 2/2006 | West et al. |
| 2006/0112438 A1 | 5/2006 | West et al. |
| 2006/0121606 A1 | 6/2006 | Ito et al. |
| 2006/0136182 A1 | 6/2006 | Vacanti et al. |
| 2006/0141617 A1 | 6/2006 | Desai et al. |
| 2006/0154361 A1 | 7/2006 | Wikswo et al. |
| 2006/0166354 A1 | 7/2006 | Wikswo et al. |
| 2006/0199260 A1 | 9/2006 | Zhang et al. |
| 2007/0026516 A1 | 2/2007 | Martin et al. |
| 2007/0084706 A1 | 4/2007 | Takayama et al. |
| 2007/0090166 A1 | 4/2007 | Takayama et al. |
| 2007/0122314 A1 | 5/2007 | Strand et al. |
| 2007/0128715 A1 | 6/2007 | Vukasinovic et al. |
| 2007/0264705 A1 | 11/2007 | Dodgson |
| 2007/0275455 A1 | 11/2007 | Hung et al. |
| 2008/0038713 A1 | 2/2008 | Gao et al. |
| 2008/0085556 A1 | 4/2008 | Graefing et al. |
| 2008/0176318 A1 | 7/2008 | Wilson et al. |
| 2008/0227176 A1 | 9/2008 | Wilson et al. |
| 2008/0233607 A1 | 9/2008 | Yu et al. |
| 2009/0023608 A1 | 1/2009 | Hung et al. |
| 2009/0123961 A1 | 5/2009 | Meyvantsson et al. |
| 2009/0148933 A1 | 6/2009 | Battrell et al. |
| 2009/0203126 A1 | 8/2009 | Hung et al. |

(56) References Cited

U.S. PATENT DOCUMENTS

| | | | |
|---|---|---|---|
| 2010/0151571 | A1 | 6/2010 | Vukasinovic et al. |
| 2010/0196908 | A1 | 8/2010 | Opalsky et al. |
| 2010/0234674 | A1 | 9/2010 | Wheeler et al. |
| 2012/0003732 | A1 | 1/2012 | Hung et al. |
| 2012/0164036 | A1 | 6/2012 | Stern et al. |
| 2013/0059322 | A1 | 3/2013 | Hung et al. |
| 2013/0081757 | A1 | 4/2013 | Hung et al. |
| 2013/0090268 | A1 | 4/2013 | Hung et al. |
| 2013/0171679 | A1 | 7/2013 | Lee et al. |
| 2013/0171682 | A1 | 7/2013 | Hung et al. |
| 2014/0057311 | A1 | 2/2014 | Kamm et al. |
| 2014/0090735 | A1 | 4/2014 | Hung et al. |
| 2014/0099705 | A1 | 4/2014 | Hung et al. |
| 2014/0287489 | A1 | 9/2014 | Lee et al. |

FOREIGN PATENT DOCUMENTS

| | | |
|---|---|---|
| EP | 0725134 | 8/1996 |
| EP | 0890636 | 1/1999 |
| GB | 1539263 | 1/1979 |
| WO | WO 91/15570 | 10/1991 |
| WO | WO 00/56870 | 9/2000 |
| WO | WO 00/60352 | 10/2000 |
| WO | WO 00/78932 | 10/2000 |
| WO | WO 01/92462 | 12/2001 |
| WO | WO 03/085080 | 10/2003 |
| WO | WO 03/098218 A1 | 11/2003 |
| WO | WO 2004/059299 A1 | 7/2004 |
| WO | WO 2004/106484 | 12/2004 |
| WO | WO 2005/035728 | 4/2005 |
| WO | 2007/008609 A1 | 1/2007 |
| WO | WO 2007/008606 | 1/2007 |
| WO | 2009/089189 A2 | 7/2009 |
| WO | 2009/102453 A2 | 8/2009 |

OTHER PUBLICATIONS

Chao et al. (2007) "Rapid frabrication of microchannels using microscale plasma activated templating (μPLAT) generating water molds." The Rolay Society of Chemistry, 7: 641-643.

Degenaar et al. (2001) "A Method of Micrometer Resolution Patterning of Primary Culture Neurons for SPM Analysys." J. Bio Chem. 367-376.

Lee et al. (2007) "Microfluidic System for Automated Cell-Based Assays." JALA. 1-19.

Lim et al. (2003) "Fabrication of Microfludic Mixers and Artifical Vasculatures Using a High-Brightness Diode-Pumped Nd:YAG Lader Direct Write Method." Lap Chip 3: 318-323.

Runyon et al. (2004) Minimal Functional Model of Hemistasis in a Biomimetic Microfluidit System. Amgew Chem. Intl. Ed. 43: 1531-1536.

Tan et al. (2003) "Microfludic Patterning of Cellular Biopolymer Matrices for Biomimetic 3-D structures." Biomedical Microdivices 5(3): 235-244.

Final Rejection mailed Apr. 11, 2014 in co-pending U.S. Appl. No. 13/436,992.

Office Action mailed Mar. 6, 2014 in co-pending U.S. Appl. No. 13/692,869.

Final Rejection mailed Apr. 4, 2014 in co-pending U.S. Appl. No. 11/994,997.

CellASIC Corporation (2012) "ONIX Application Note: microincubator for long term."

Hung et al. (2005) "Continuous perfusion microfludic cell culture array for high-throughput cell-bases assays." Biotechnigues and Bioengineering 89(1): 1-8.

Lee et al. (2007) "Microfluidic System for Automated Cell-Based Assays." Lab Chip 9(1): 164-166.

Lee et al. (2007) "Microfluidic System for Automated Cell-Based Assays." JALA 12(6): 363-367.

Ong et al. (2008) "A gel-free 3D microfluidic cell culture system." Biomaterials 29(22): 3237-3244.

International Preliminary Report on Patentability mailed Jun. 12, 2014 in co-pending PCT application No. PCT/US2012/067632.

Engineering Aspects of Food Biotechnology, Chapter 5, CRC Press: Boca Raton, FL, 2004, copyright 2014, p. 127, "Meet the Stem Cells; Production of Cultured Meat from a Stem Cell Biology Perspective", Brinkhof, et al., 3 pages.

Office Action mailed May 13, 2014 in co-pending U.S. Appl. No. 13/011,857.

Notice of Allowance mailed Jul. 2, 2014 in co-pending U.S. Appl. No. 13/692,869.

Final Rejection mailed Jun. 25, 2014 in co-pending U.S. Appl. No. 13/761,130.

EP Search Report for application No. 06786499.1 dated Apr. 3, 2012.

Lab on a Chip, 2007, vol. 7, pp. 763-769, "A hydrogel-based microfluidic device for the studies of directed cell migration", Cheng, et al.

Lab on a Chip, 2009, vol. 9, p. 1797-1800, "Selective and tunable gradient device for cell culture and chemotaxis study", Kim, et al.

Biomed Microdevices (2008), vol. 10, pp. 499-507, "Microfluidic switching system for analyzing chemotaxis responses of wortmannin-inhibited HL-60 cells", Liu, et al.

Lab on a Chip, 2007, vol. 7, pp. 1673-1680, "Gradient generation by an osmotic pump and the behavior of human mesenchymal stem cells under the fetal bovine serum concentration gradient", Park, et al.

Notice of Allowance mailed Jan. 13, 2014 in co-pending U.S. Appl. No. 13/602,328.

Notice of Allowance mailed Dec. 23, 2013 in co-pending U.S. Appl. No. 13/602,331.

Office Action mailed Dec. 31, 2013 in co-pending U.S. Appl. No. 13/761,130.

International Search Report and Written Opinion mailed Apr. 9, 2009 in PCT application No. PCT/US06/26364 (corresponding to U.S. Appl. No. 11/994,997).

International Search Report and Written Opinion mailed Jul. 30, 2009 in PCT application No. PCT/US2009/030168.

Extended European Search report mailed Oct. 21, 2013 in European patent application No. EP 09701350.

International Search Report mailed May 14, 2013 in PCT application No. PCT/US2013/024999.

International Search Report mailed Mar. 19, 2013 in PCT application No. PCT/US2012/067632.

Lab Chip, 2005, vol. 5, No. 4, pp. 401-406, "Human neural stem growth and differentiation in a gradient-generating microfluidic device", Chung, et al.

Lab Chip, 2008, vol. 8, No. 1, pp. 34-57, "Biomolecular gradients in cell culture systems", Keenan, et al.

Biotechnology and Bioengineering, vol. 97, No. 5, Aug. 1, 2007, pp. 1340-1346, "An Artificial Liver Sinusoid With a Microfluidic Endothelial-Like Barrier for Primary Hepatocyte Culture", Lee, et al.

Lab Chip, 2009, vol. 9, No. 1, pp. 164-166, "Dynamic cell culture: a microfluidic function generator for live cell microscopy", Lee, et al.

Office Action mailed Apr. 25, 2013 in co-pending U.S. Appl. No. 13/602,328.

Notice of Allowance mailed Oct. 28, 2013 in co-pending U.S. Appl. No. 13/602,328.

Office Action mailed Feb. 22, 2013 in co-pending U.S. Appl. No. 13/602,331.

Office Action—Restriction—mailed Jul. 13, 2011 in co-pending U.S. Appl. No. 12/348,907.

Office Action mailed Dec. 23, 2011 in co-pending U.S. Appl. No. 12/348,907.

Final Rejection mailed Sep. 17, 2012 in co-pending U.S. Appl. No. 12/348,907.

Office Action Nov. 28, 2012 in co-pending U.S. Appl. No. 13/011,857.

Final Rejection mailed Aug. 14, 2013 in co-pending U.S. Appl. No. 13/011,857.

Office Action—Restriction—mailed Feb. 22, 2013 in co-pending U.S. Appl. No. 13/436,992.

Office Action mailed Sep. 6, 2013 in co-pending U.S. Appl. No. 13/436,992.

Office Action—Restriction—mailed Oct. 16, 2013 in co-pending U.S. Appl. No. 13/692,869.

(56) References Cited

OTHER PUBLICATIONS

Office Action—Restriction—mailed Oct. 7, 2013 in co-pending U.S. Appl. No. 13/761,130.
Office Action—Restriction—mailed Mar. 9, 2011 in co-pending U.S. Appl. No. 11/994,997.
Office Action mailed Jul. 18, 2011 in co-pending U.S. Appl. No. 11/994,997.
Final Rejection mailed Feb. 8, 2012 in co-pending U.S. Appl. No. 11/994,997.
Office Action mailed Sep. 11, 2013 in co-pending U.S. Appl. No. 11/994,997.
Notice of Allowance mailed Nov. 13, 2013 in co-pending U.S. Appl. No. 13/602,331.
Lab Chip, 2005, vol. 5, pp. 44-48, "A novel high aspect ratio microfluidic design to provide a stable and uniform microenvironment for cell growth in a high throughput mammalian cell culture array", Hung, et al.
Office Action mailed Jan. 26, 2015 in co-pending U.S. Appl. No. 11/994,997.
Notice of Allowance mailed Dec. 22, 2014 in co-pending U.S. Appl. No. 12/348,907.
Office Action mailed Nov. 6, 2014 in co-pending U.S. Appl. No. 13/436,992.
Office Action mailed Oct. 27, 2014 in co-pending U.S. Appl. No. 13/761,130.
Final Rejection mailed Oct. 20, 2014 in co-pending U.S. Appl. No. 13/011,857.
Office Action mailed Sep. 15, 2014 in co-pending U.S. Appl. No. 14/081,314.
Advisory Action mailed Jul. 24, 2014 in co-pending U.S. Appl. No. 11/994,997.
Final Rejection mailed Mar. 23, 2015 in co-pending U.S. Appl. No. 13/436,992.
Office Action mailed May 13, 2015 in co-pending U.S. Appl. No. 14/053,688.
Notice of Allowance mailed May 6, 2015 in co-pending U.S. Appl. No. 13/761,130.
Notice of Allowance mailed May 4, 2015 in co-pending U.S. Appl. No. 14/081,314.
European communication dated Jul. 28, 2015 in co-pending European patent application No. 12852539.1.
Notice of Allowance mailed Oct. 13, 2015 in co-pending U.S. Appl. No. 12/348,907.
Office action mailed Oct. 6, 2015 in co-pending U.S. Appl. No. 13/011,857.
Office Action mailed Jun. 19, 2015 in co-pending U.S. Appl. No. 14/221,615.
Notice of Allowance mailed Jun. 22, 2015 in co-pending U.S. Appl. No. 11/994,997.
Notice of Allowance mailed Jul. 31, 2015 in co-pending U.S. Appl. No. 13/692,869.
Notice of Allowance mailed Aug. 4, 2015 in co-pending U.S. Appl. No. 13/761,130.
Notice of Allowance mailed Aug. 24, 2015 in co-pending U.S. Appl. No. 14/081,314.
Notice of Allowance mailed Sep. 21, 2015 in co-pending U.S. Appl. No. 14/053,688.
Final Rejection mailed Mar. 11, 2016 in co-pending U.S. Appl. No. 13/436,992.
Japanese communication, with English translation, dated Nov. 17, 2015 in co-pending Japanese patent application No. 2015-503203.
Keenan et al., "A new method for studying gradient-induced neutrophil desensitization based on an open microfluidic chamber", Lab Chip, 2010, vol. 10, pp. 116-122.
Lee et al., "Microfluidic Systems for Live Cell Imaging", Methods in Cell Biology, 2011, vol. 102, pp. 77-103.
Notice of Allowance mailed Jan. 13, 2016 in co-pending U.S. Appl. No. 14/053,688.
Notice of Allowance mailed Jan. 20, 2016 in co-pending U.S. Appl. No. 12/348,907.
Office action mailed Nov. 20, 2015 in co-pending U.S. Appl. No. 13/436,992.
Notice of Allowance mailed Jan. 6, 2016 in co-pending U.S. Appl. No. 14/221,615.
Notice of Allowance mailed Feb. 4, 2016 in co-pending U.S. Appl. No. 13/161,130.
Notice of Allowance mailed Feb. 22, 2016 in co-pending U.S. Appl. No. 14/081,314.
Notice of Allowance mailed Apr. 27, 2016 in co-pending U.S. Appl. No. 14/053,688.
Notice of Allowance mailed Apr. 7, 2016 in co-pending U.S. Appl. No. 13/011,857.
Notice of Allowance mailed Apr. 11, 2016 in co-pending U.S. Appl. No. 14/221,615.

* cited by examiner

Press molding
with 3mm
PMMA sheet &
cure at 60°C for
2 hours

Release
microfluidic

Laser cut fluidic
reservoirs

Bonded to #1
coverglass

Load particles
and analyze

Fig. 14A
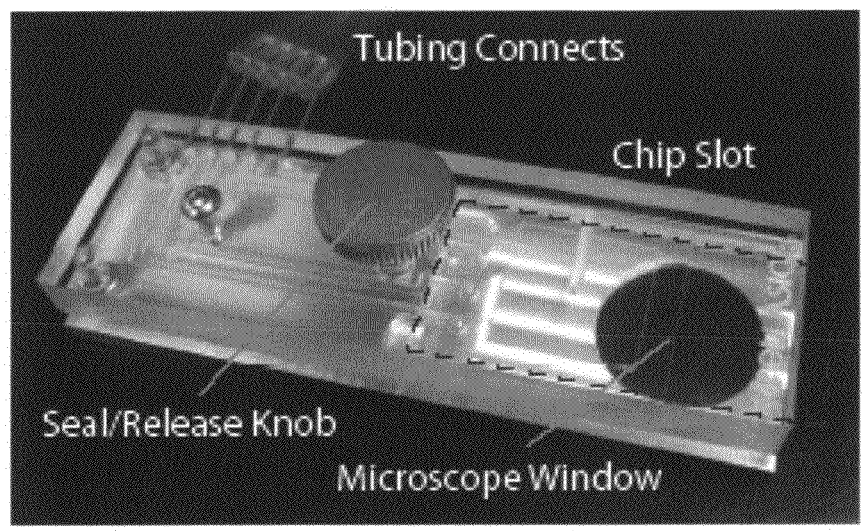
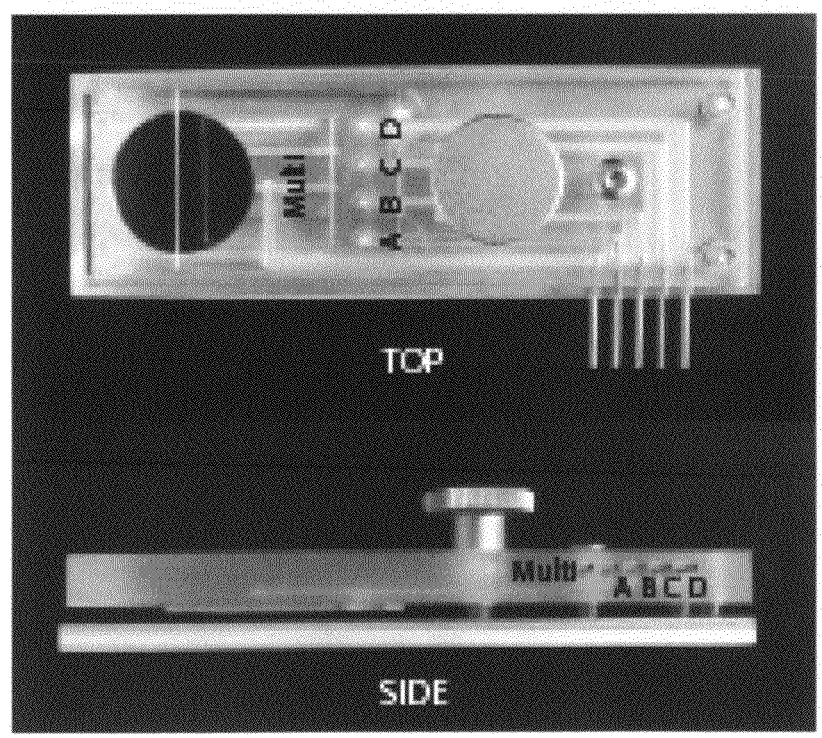
Fig. 14B

MICROFLUIDIC PARTICLE ANALYSIS METHOD, DEVICE AND SYSTEM

This application claims priority to U.S. Provisional Patent Application No. 60/900,651 filed on Feb. 8, 2007, which is incorporated herein in its entirety by reference.

FIELD

The device and method relate to microfluidic particle analysis. The device is designed for trapping particles for solution analysis. Exemplary particles include beads and cells.

BACKGROUND

Particle-based science and technology is an important aspect of biomedical and clinical research. Inorganic particles such as quantum dots and beads have found applications in bio-imaging and point-of-care diagnosis. These particles can further be conjugated with other materials such as proteins or DNAs for biosensors and bioassays. Living particles such as cells, viruses and bacteria are commonplace in everyday biological experiments. Through analysis of their molecular and cellular properties using techniques such as DNA sequencing, protein mapping and high content screening, these particles have greatly advanced the development of the biological sciences.

The most common particle analysis apparatus is the flow cytometer, where particles with fluorescent tags are hydrodynamically focused into a stream and excited by laser beams. The emitted fluorescence from the tags are collected by photodetectors and analyzed to extrapolate information about the biological properties of each individual particle. There are three major drawbacks of the system: 1) the system is expensive and bulky. 2) the particles can not be analyzed over time due to the single pass nature of the flow cytometer. 3) it does not resolve subcellular localization of fluorescent signals.

In order to conduct detailed analysis of the particles, it is desired to trap these particles in specific locations so they don't displace due to the forces of fluid flow, shear stress or thermal agitation during the course of the experiment. Microfluidic devices are ideal candidates for particle analysis because of their compact size, low reagent consumption and laminar flow nature. One common method of trapping particles is to use dielectrophoresis, where electrodes and electric fields are used to generate dielectrophoretic forces on particles; however, the particles trapped using this method can still rotate, and are subject to displacement when flows are introduced. In addition, the fabrication of electrodes into the device significantly increases the cost. Using a sieve at a size smaller than the particles can serve as a particle trap; however, the particles will be packed into clumps, making it difficult to analyze.

The potential advantages of a trapped particle array device have been realized to a limited extent in the prior art. Various limitations associated with prior art devices include (i) difficulty in preventing microfluidic structures from being blocked by particles within the structures, (ii) inability to trap the particles so they won't be displaced by fluidic flows, (iii) inability to provide different solutions to the particles at different times for rapid assay.

It would therefore be desirable to provide a microfluidic particle trapping device capable of more fully realizing the advantages noted above in a high throughput particle analysis system.

SUMMARY

In one aspect, a microfluidic particle analysis device is provided comprising
 a microfluidics body,
 formed in said body, a microfluidics channel for receiving particles at an upstream region thereof,
 the channel having a deformable wall portion that defines a particle-capture region, and which is responsive to a change in fluid pressure applied thereto, to selectively vary the particle-flow dimensions of said capture region,
 wherein particles having a given size may be selectively retained in said capture region.

In one embodiment, the deformable wall portion is expandable in response to a positive fluid pressure applied within the channel. In another embodiment, said deformable wall portion is expandable in response to a negative pressure applied to a cavity communicating with said wall portion, external to said channel. In some embodiments, said wall portion is deformable from a relaxed condition, at which particles of a selected size are prevented from entering the particle capture region, to a first expanded position at which particles of a selected size may enter and flow through the capture region.

In a particular embodiment, said capture region is defined by a cavity in said deformable wall portion, movement of the wall portion from its relaxed to its first expanded condition allows particles of a selected size to enter and flow through said cavity, and movement of said wall portion from its first expanded condition to its relaxed condition allows such particles to be trapped within said cavity in said capture region.

In another particular embodiment said wall portion is deformable from a relaxed condition, at which particles of a selected size are prevented from entering the particle capture region, to a first expanded position at which particles of a selected size may enter the capture region, and from the first expanded condition to a second expanded position in which the particles become trapped within said capture region.

Some embodiments comprise a microfluidic mesh in fluid contact with the microfluidic passageway, wherein the mesh prevents the passage of particles from the microfluidic passageway to a channel outlet downstream of the particle capture region. Some embodiments include an array of such channels and associated wall portions. In some embodiments, the microfluidic passageway has a plurality of longitudinally spaced capture regions, each defined by a deformable wall portion, and designed for trapping particles of different diameters.

The deformable wall portion is formed of a deformable polymer selected from the group consisting of polydimethylsiloxane (PDMS), polyisoprene, polybutadiene, polychloroprene, polyisobutylene, poly(styrene-butadiene-styrene), polyurethane, and silicone.

In some embodiments, the selectively retained (trapped) particles are addressed with a solution. In other embodiments, the selectively retained particles are addressed with a plurality of solutions in series. In particular embodiments, the solution comprises a drug, a reagent, a nutrient, blood, or serum.

In some embodiments, the solution displaces the selectively retained particles by no more than 10% of the size of the particles. In some embodiments, the solution provides fluid exchange in less than 10 seconds.

In another aspect, methods are provided for trapping particles using a microfluidic channel having a deformable wall portion.

These and other objects and features of the invention will become more fully understood when the following detailed description of the invention is read in conjunction with the accompanying drawings.

BRIEF DESCRIPTION OF THE FIGURES

FIGS. 14A-14C show a control box and a manifold for use with the microfluidic particle analysis device.

DETAILED DESCRIPTION

A. Definitions

Figures 1A, 1B, 1C:
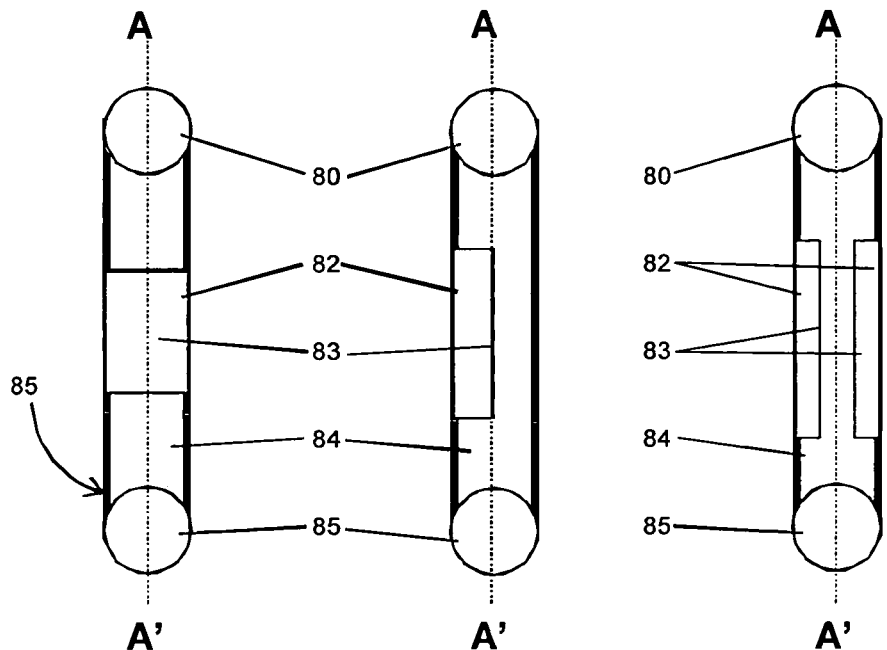
FIGS. 1A-C show a top (A) and side (B and C) views of a microfluidic particle trapping device with a cross-section defined by the line A-A'.

Prior to describing the present device and methods, the following terms and phrases are defined:

A "particle" refers to living or dead cells, such as mammalian, yeast, insect, and bacterial cells; beads such as polymer beads and metal beads; or other physical entities that may be trapped for analysis in accordance with the methods and device described, herein. Such particles have an average minimum diameter of between about 100 nm to about 50 μm, preferably between about 1 μm to about 30 μm, more preferably between about 2 μm to about 20 μm, and even between about 3 μm to about 10 μm. Some particles can be coated or functionalized with additional layers of materials, e.g, gold-coated or antibody-coated polystyrene beads.

The "size" of a particle generally refers to its average or typical diameter. The device and methods are for use with substantially spherical particles or particles having a less than a 2-fold and even less than a 1.5-fold difference in the major and minor elliptical axis of non-spherical particles. The particles size generally excludes such extracellular structures as flagella, cilia, pilli, pseudopods, processes, or other readily deformable structures.

A "microchannel" or "microfluidic channel" refers to a micron-scale conduit for carrying fluid, solvents, solutes, and suspended micron-scale particles. A microchannel typically has a rectangular, e.g., square cross-section, with preferred width and depth dimensions of between about 10 μm to about 500 μm, and about 0.5 μm to about 50 μm, respectively. Micro-channels may also be elliptical or round. Fluids flowing in the microchannels may exhibit microfluidic behavior such as low Reynolds number and low turbulence. The microchannel channel has an internal dimension (referred to as a particle-flow dimension), defined by height H, which determines the maximum particle size that can enter the microchannel channel.

Where the microchannel includes a deformable wall portion, the deformable wall portion typically defines the particle-flow dimension, which is indicated as height h. This dimension is adjustable, using pneumatic pressure, from a relaxed condition, which prevents the passage of particles of a preselected size, to an expanded position, which allows the passage of these particles.

A "channel segment" is a particular structural or functional portion of a microchannel device, optionally in combination with one or more ports.

A "microfluidic body" refers to a device having various stations, wells, or reservoirs connected by micron-scale microchannels in which fluids will exhibit microfluidic behavior in their flow through the channels.

As used herein, "fluid contact" means arranged so as to allow fluid to flow from one vessel, chamber, or conduit to another, as described herein and as understood in the art. Fluid contact is synonymous with "fluid communication."

The terms "elastomer" and "elastomeric" should be given their standard meaning as used in the art. Allcock et al. (Contemporary *Polymer Chemistry*, 2nd Ed.) describes elastomers as polymers existing at a temperature between their glass transition temperature and liquefaction temperature. Elastomers generally deform under force and return to their original shape when the force is removed. The elasticity exhibited by elastomeric materials can be characterized by a Young's modulus. Elastomers for use with the microfluidic particle trapping device include but are not limited to polydimethylsiloxane (PDMS), polyisoprene, polybutadiene, polychloroprene, polyisobutylene, poly(styrene-butadiene-styrene), and members of the polyurethane and silicone families. Additional examples are provided in U.S. Pat. No. 7,144,616, which is incorporated herein by reference in its entirety for all purposes.

As used herein, "deformable" means readily changing shape or dimensions in response to stress or strain. Stress or strain includes fluid and pneumatic pressure. Upon the application of stress, deformable structures change shape from a relaxed condition to an expanded, compressed, bent, twisted, or distorted condition.

As used herein, "trapping" or "capturing" are used interchangeably to mean substantially immobilizing or confining between two elastomeric layers and/or between an elastic layer and an inelastic layer. A particle trapping region is synonymous with a particle capture region.

"Substantial fluid exchange" means replacement of fluid by ingress of a different fluid, as in washing particles immobilized in a column. Fluid exchange is substantial when at least 90%, and preferably at least 95% of fluid is replaced.

As used herein, a "port" is a point of ingress or egress for fluids and or gas. Fluids and gases may be provided to a port under pressure (including both positive and negative pressure), and may be delivered to a location within a microfluidic particle trapping device via microchannels.

As used herein, "pneumatic pressure" means pressure originating from air pressure, although air (or an inert or non-interfering gas) and/or fluid may contact the port of the device. Preferred pneumatic pressures are from about 0.1 pound per square inch (psi) to about 10 psi, from about 0.5 psi to about 7 psi, and from about 1 psi to about 5 psi. Exemplary pressures include, e.g., 1, 2, 3, 4, and 5 psi.

As used herein, "fluid pressure" means pressure exerted by a fluid, although the fluid pressure may be the result of pneumatic, hydraulic, gravitational, or capillary pressure. Preferred fluid pressures are from about 0.1 pound psi to about 10 psi, from about 0.5 psi to about 7 psi, and from about 1 psi to about 5 psi. Exemplary pressures include, e.g., 1, 2, 3, 4, and 5 psi.

The "substrate" is the base of the device, and may be transparent, at least under the trapping regions, to allow their visualization by microscopy or other optical methods. Alternatively, the substrate may include a light filtering or contrast-enhancing agent to assist in the assay. Examples of suitable substrates are glass (exemplified herein) and polycarbonate. Many other materials are suitable, depending on the application, and soft lithographic bonding on a substrate is known in the art (see, e.g., U.S. Pat. No. 7,144,616, which is incorporated herein by reference in its entirety for all purposes).

As used herein, the "height (h, h'. h''', etc.)" of the microfluidic channel trapping/capturing region is the particle-flow dimension corresponding to the distance separating the inside surface of the deformable wall portion from the opposite wall of the microfluidic channel. This internal dimension determines the diameter of the particles that can be trapped by the device As used herein, "height H" of a microfluidic channel is the particle-flow dimension. Microfluidic channels having deformable wall portions have a "height h", which is the particle flow-dimension defined by the deformable wall portions. "H''" and "h''''" are sometimes used to indicate the h has changed with respect to another drawing.

B. Particle Trapping Mechanisms

The device and method are best described with reference to the accompanying Figures. Common features are generally assigned the same numbers.

FIGS. 1A-C show a top (A) and side (B and C) views of simple embodiment of the microfluidic particle trapping device. A microfluidic body 86 has an inlet port 80 and outlet port 85 in fluid contact with a microfluidic channel. The microchannel has a particle trapping region 82 with a deformable wall portion 83, in fluid contact with secondary microchannel segments, e.g., 84, which are in contact with the ports 80 and 85. The secondary channel segments may be relatively nondeformable as suggested by the use of heavier lines.

Figure 1D:
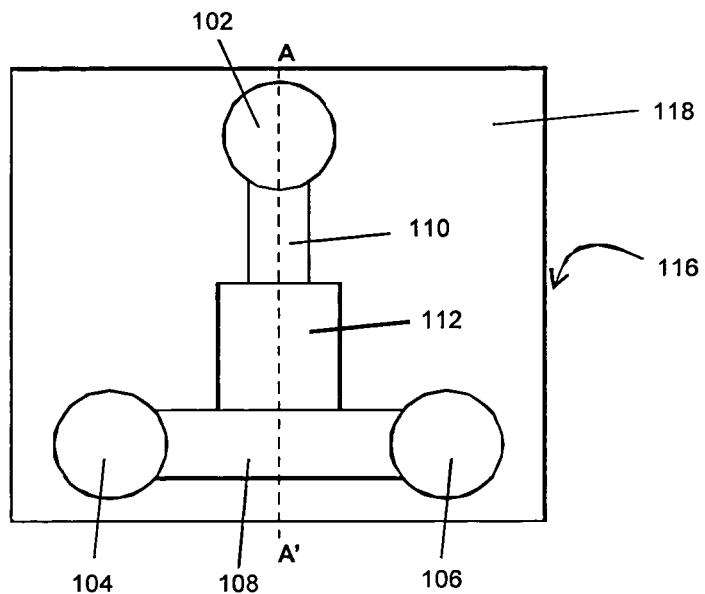
FIG. 1D shows a plan view of an embodiment of the microfluidic particle trapping device with three reservoirs and a cross-section defined by the line A-A'.

FIG. 1D shows a top view of an embodiment of the microfluidic particle trapping device for particle analysis. The microfluidic body 116 is bonded to a substrate 118, such as a glass or plastic. The particle inlet port 102, solution inlet port 104, and solution outlet port 106, are in fluid contact with a microfluidic channel having a particle trapping region 112, via secondary microchannels 108 and 110. The particle inlet port and solution inlet port in combination with the associated microchannels, are generally referred to as inlet channel segments. The solution outlet port 106, in combination with the associated microchannels, is generally referred to as an outlet channel segment. The ports are generally adapted for receiving pneumatic pressures. As used herein, the particle inlet port 102 is upstream of the particle trapping region 112, while the solution inlet port 104, and solution outlet port 106 are downstream. Note that the arrangement of the various ports is not critical in some embodiments. The terms "upstream" and "downstream" are used to describe flow characteristics in different embodiments.

Figure 2A:
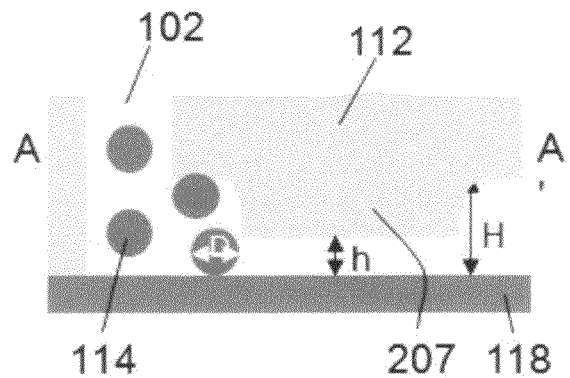
FIGS. 2A-2C show cross-sectional views (A-A' in FIG. 1) of an embodiment of the microfluidic particle trapping device in different stages of operation, and having a microfluidic channel of height H', an trapping region internal dimension of height h'. (A) The deformable wall portion is in the relaxed condition, wherein the particle flow dimension (i.e., internal dimension h) is less than the diameter of the particles. (B) The deformable wall portion is in the expanded condition, wherein the particle flow dimension is greater than the particle diameter, allowing the particles to enter the microfluidic channel. (C) The deformable wall portion in the relaxed condition to trap the particles in the microfluidic channel.
Figure 2B:
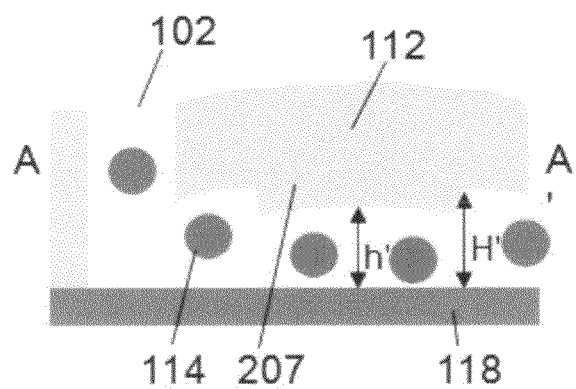
Figure 2C:
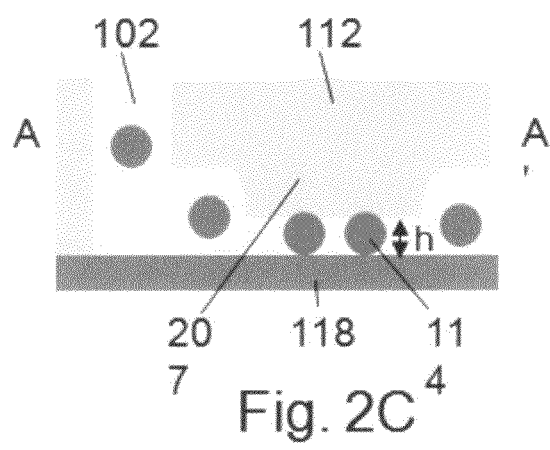

FIGS. 2A-2C show cross-sectional views (A-A') of the microfluidic particle trapping device in different stages of operation. The deformable wall portion 207 of the particle trapping region 112 is preferably made of an elastomer, such as PDMS (polydimethylsiloxane), such that the deformable wall changes from a relaxed condition to an expanded position in response to fluid pressure (e.g., as provided by pneumatic pressure). As shown in FIG. 2A, an internal dimension (height "h") is defined by the position of the deformable wall portion 207 of the particle trapping region 112. The secondary microchannels (i.e., 108 and 110) are designed such that their height ("H") is larger than the particle diameter. Although the deformable wall portions are generally depicted as having thicker channel-wall sections than the adjacent microchannel, the deformable wall portions may have thicker or thinner walls than the adjacent microchannel.

As shown in FIG. 2B, when a first pneumatic pressure is applied to the inlet port 102, the fluid pressure in the microfluidic channel increases and h' defined by the deformable wall portion 207 of the particle trapping region 112 becomes greater than the diameter of the particles 114, allowing the particles to move freely within the trapping region 112. When the inlet port 102 is pressurized to a second pneumatic pressure, as depicted in FIG. 2C, the fluid pressure in the microfluidic channel decreases, the deformable wall portion 207 defines a height of less than the particle diameter. Particles 114 present within the trapping region 112 are trapped (i.e., captured) by being sandwiched between the deformable wall of the microfluidic channel 207 and the bottom surface (substrate) 118 of the microfluidic device. Since the deformable wall is typically biased toward trapping the particles, the second pneumatic pressure may be zero (i.e., the same as the pressure external to the device), in which case, applying a second pneumatic pressure means allowing the deformable wall to return to its relaxed state or condition.

In other embodiments, the deformable wall portion is first deformed from a relaxed condition, at which particles of a selected size are prevented from entering the particle capture region, to a first expanded position, in which particles of a selected size may enter the capture region, and from the first expanded position to a second expanded position, in which the particles become trapped within said capture region. Pressure to drive the deformable wall portion from the first expanded position to a second expanded position may be provided via the ports or applied to the external surface of the microfluidic channels (see infra).

The trapped particles may then be exposed to (i.e., addressed with) a solution from port 104, e.g., by pressurizing the port with sufficient pressure to cause the solution to flow through the trapping region 112 to contact the particles 114, but insufficient to deform the deformable wall portion, allowing the particles to move or escape. The trapped particles may also be address with multiple solutions, for example, in a series or a particular sequence.

In preferred embodiments, addressing the trapped particles with a solution causes the particles to be displaced by less than about 10% of the size of the particles. For example, a trapped particle of about 10 µm diameter is displaced by only about 1 µm.

Figure 3A:
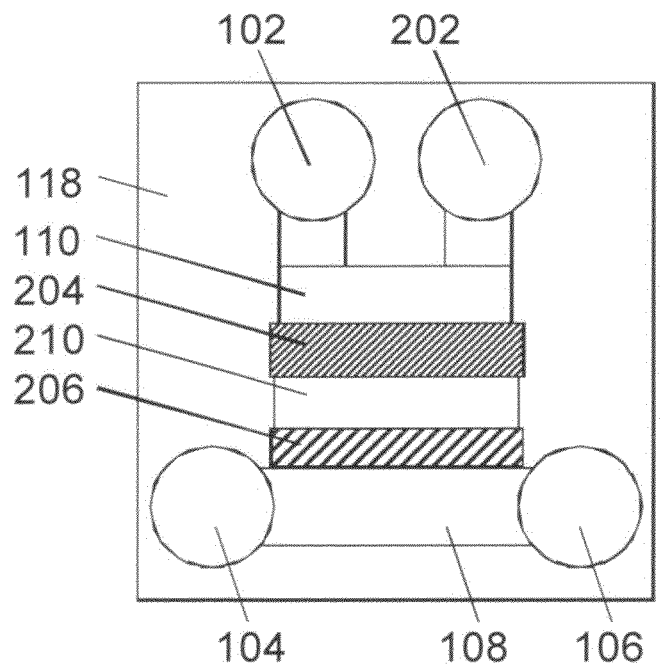
FIGS. 3A and 3B show an embodiment of the device with an additional particle outlet port, multiple trapping regions with different heights, and a sieve to prevent particles from entering the solution ports. (A) Plan view. (B) Cross-section A-A'.
Figure 3B:
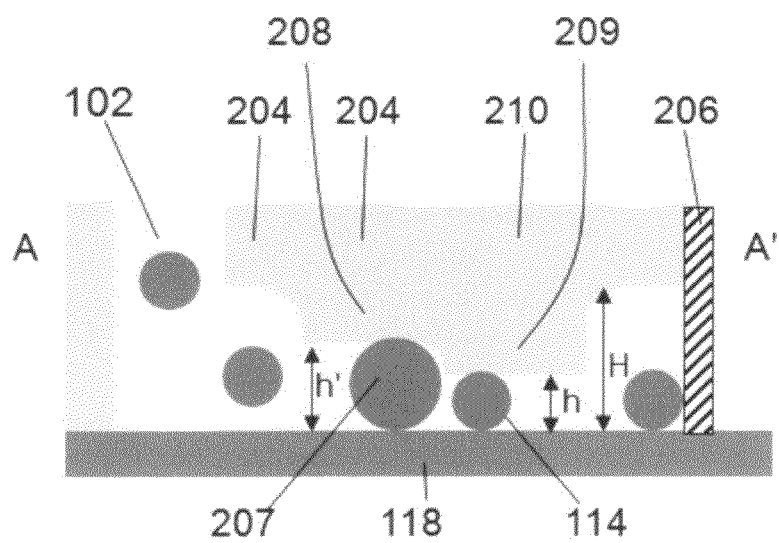

FIGS. 3A and 3B illustrate a further embodiment of the microfluidic particle trapping device 116 having additional features, which may be used alone or in combination. First, the embodiment has an additional port 202 in fluid contact with the inlet port 102. Following the release of pressure and the trapping of particles in the trapping region, the additional port 202 allows particles outside the trapping region 112 to be flushed from the microfluidic particle trapping device by means of fluid flow from additional port 202 to inlet port 102 or from inlet port 102 to additional port 202. Depending on the direction of flow, the additional port 202 is considered part of the inlet channel segment or outlet channel segment.

Second, the embodiment shown in FIGS. 3A and 3B has a first and second trapping region 204 and 210, respectively, with independent deformable walls portion 208 and 209, respectively, or sharing a common deformable wall portion that defines different particle-flow dimensions. According to this embodiment, the microfluidic channel has dimensions h" and h''', which are adjustable by pneumatic pressure for trapping particles having different diameters. The particle trapping device may have any number of longitudinally spaced trapping/capture regions, for example, 1, 2, 3, 4, 5, etc. In some embodiments, the particle-flow dimension decreases with each successive trapping segment, such that the particle-flow dimension of the trapping segment most proximal to the particle inlet 102 is greatest and that most distal to the particle inlet is least.

Third the embodiment shown in FIGS. 3A and 3B further incorporates a microfluidic mesh region 206 having a mesh size less than the diameter of the particles to prevent the particles leaving the trapping region 204 and 210 (i.e., flowing through the trapping region and out the solution inlet port 104 or outlet port 106. The microfluidic mesh region 206 is particularly useful when multiple solution inlet ports 104 are arrayed along a common solution-introduction channel 104. In such cases, the mesh region 206 prevents particles introduced to one particle inlet port from migrating through the adjacent trapping layer, and then exiting the device downstream of the trapping layer. The mesh region 206 is shown in contact with the substrate 118 but may be spaced apart so long as the particles do not escape. A trapping layer with a small particle flow dimension may also be used to prevent particles from leaving the trapping region.

Figure 4A:
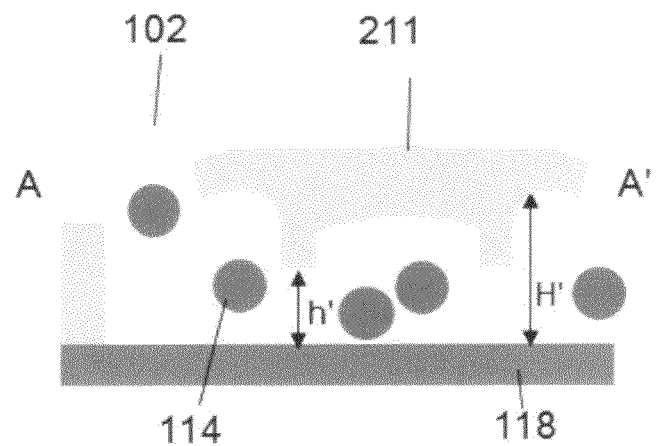
FIGS. 4A and 4B show cross-sectional views of an embodiment of the device in different stages of operation, and having a deformable wall with a cavity. (A) The device is at the first pneumatic pressure to show that the internal dimension (h') is greater than the diameter of the particles. (B) The device is at the second pneumatic to trap the particles in the cavity of the deformable the deformable wall portion.
Figure 4B:
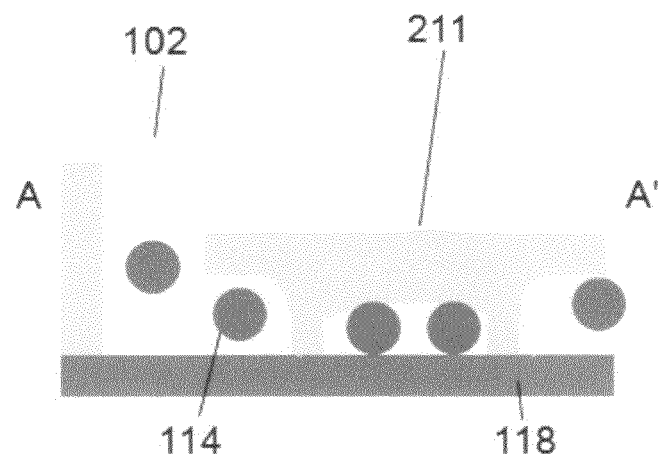

FIGS. 4A and 4B show cross-sectional views of an embodiment of the microfluidic particle trapping device having a deformable wall portion with a cavity 211. At the first pneumatic pressure, with the deformable wall portion in the expanded condition, the internal dimension (h') is greater than the diameter of the particles 114, allowing the particles from the particle inlet port 102 to flow freely under the deformable wall portion. At the second pneumatic pressure, with the deformable wall portion in the relaxed condition, the particles are trapped between the deformable wall portion 211 and the substrate/base 118.

Figure 5A:
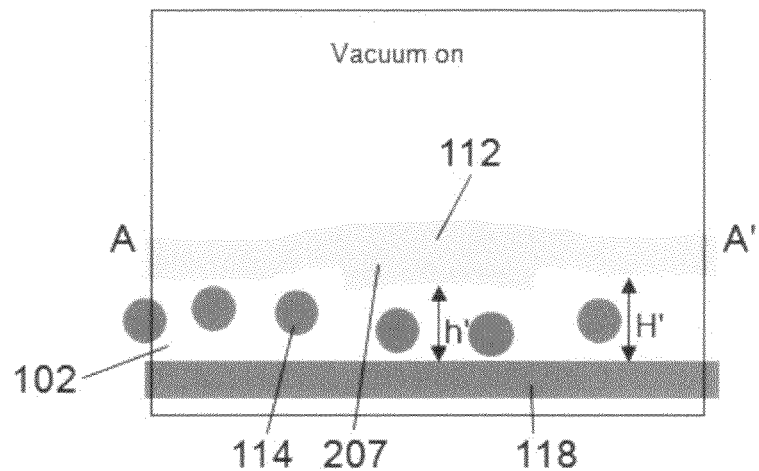
FIGS. 5A and 5B show cross-sectional views of an embodiment of the device for us with a vacuum source. (A) When vacuum is applied, the internal dimension (h') is greater than the diameter of the particles. (B) When vacuum is released, the particles are trapped by the deformable wall portion.
Figure 5B:
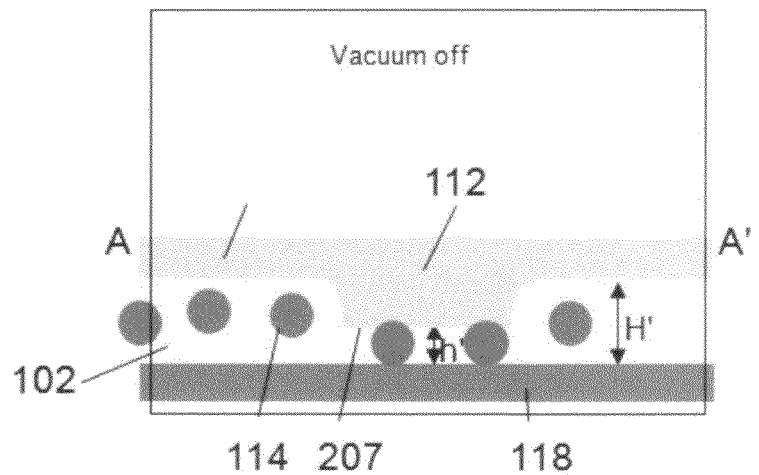

The previous embodiments of the device are described with reference to applying a positive pressure to the microfluidic channel via the ports, thereby increasing the pressure inside the channel relative to the pressure outside the channel, and causing the deformable wall portion to change shape. In another embodiment, the pressure in the microfluidic channel is increased, relative to the pressure outside the chamber, by exposing the outside surface of the microfluidic chamber, adjacent to the deformable wall portion, to a negative pressure, i.e., a vacuum. This may be accomplished by applying localized vacuum to a suitably adapted embodiment of the microfluidic device, or by placing the microfluidic body in a vacuum chamber, while the ports remain exposed to atmospheric pressure. This embodiment is shown in FIGS. 5A and 5B.

The deformable wall portion 207, trapping portion 112, substrate 118, are essentially as described. The format of the particle inlet port 102 is different. Surfaces exposed to vacuum are inside the box. Outside the box is atmospheric pressure (or at least less vacuum pressure than inside the box). When vacuum is applied, the internal dimension (h') is greater than the diameter of the particles 114. When vacuum is released, the particles 114 are trapped by the deformable wall portion 207.

Figure 6:
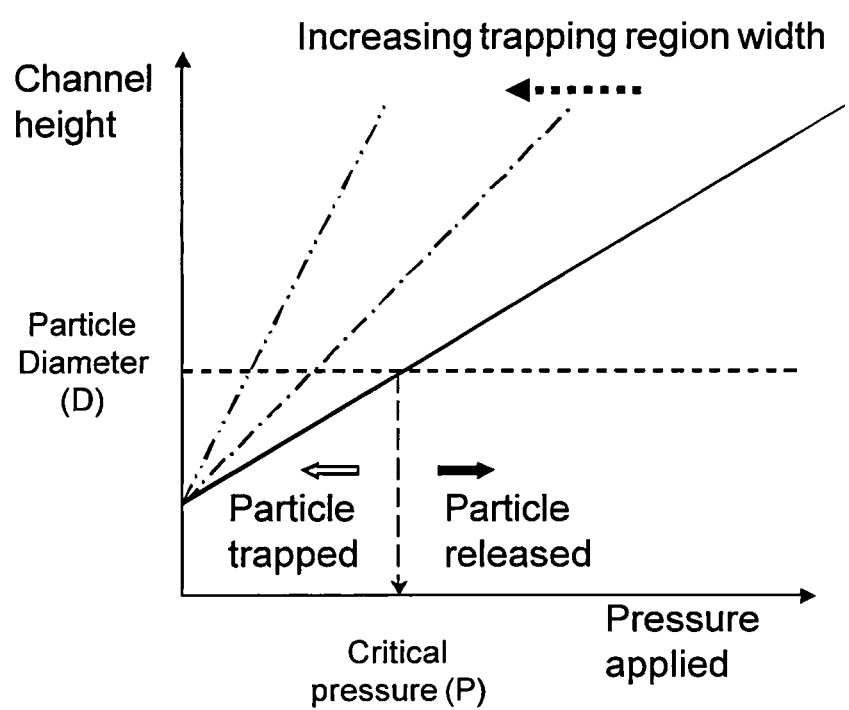
FIG. 6 is a graph showing the relationship between internal dimension of the microfluidic channel (channel height h') as a function of pneumatic pressure (P).

FIG. 6 is a graph showing the relationship between the height (h) of the trapping region and the pneumatic pressure applied to the device. When a pneumatic pressure (x-axis) is applied, e.g., via the inlet port or solution port, the fluid pressure in the microfluidic channel changes and the deformable wall of the trapping region experiences height deformation (y-axis). Generally, the greater the positive pressure in the trapping region, the greater the height (h) of the trapping region. The critical pressure is the pressure at which the height of the trapping region is substantially equal to the diameter of the particle. When the applied pressure is greater than the critical pressure, the particles can move freely within or through the trapping region. When the applied pressure is less than the critical pressure, the particles within the trapping region are trapped. One skilled in the art will recognize that there are numerous ways to produce the small pressure differential required for deforming a deformable wall.

C. Yeast Cell Imaging Device

Figure 7:
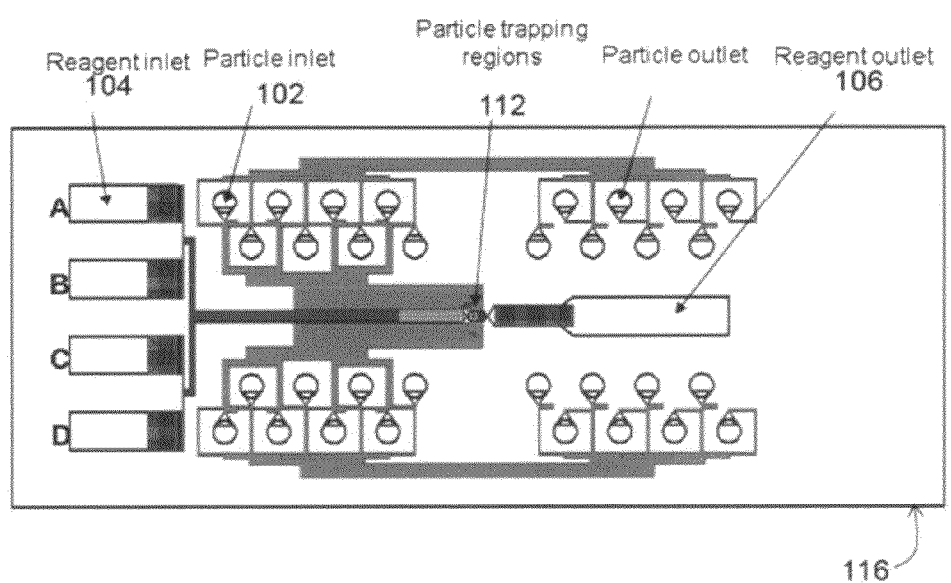
FIG. 7 shows a drawing of an embodiment of the device for analyzing 16 different particles with 4 different solution-switching functions.
Figure 8:
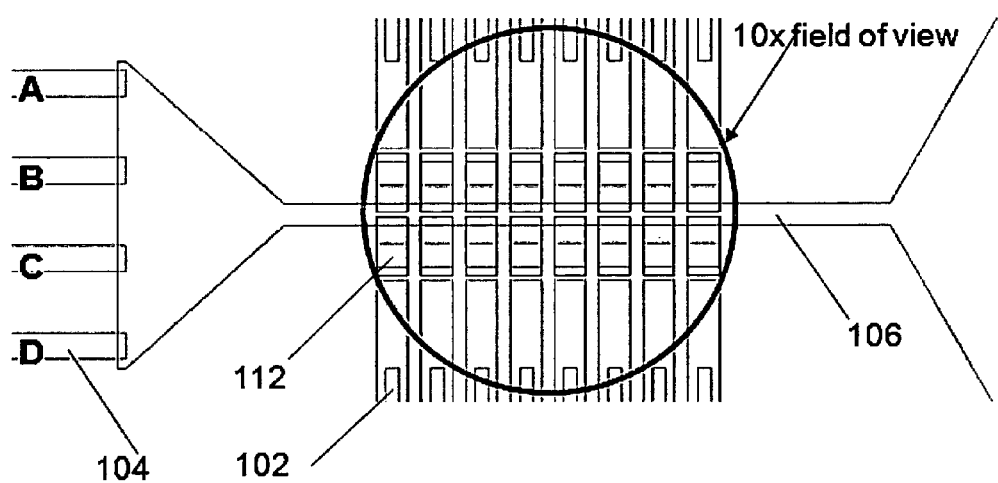
FIG. 8 shows the particle trapping region in an embodiment of the device.

FIG. 7 is a schematic diagram of another embodiment of the microfluidic particle trapping device. The trapping regions are placed close to each other for the convenience of microscopic analysis. The device provides up to four solution-switching stations (e.g., solution inlet ports 104, A-D) for analyzing the trapped particles. FIG. 7 shows a more detailed view of the particle trapping regions 112. In this example, there are 16 particle trapping regions 112 inside the single field of view of a 10× objective. A particle inlet port 102, solution inlet port 104, and solution outlet port 106 are indicated.

Figure 9:
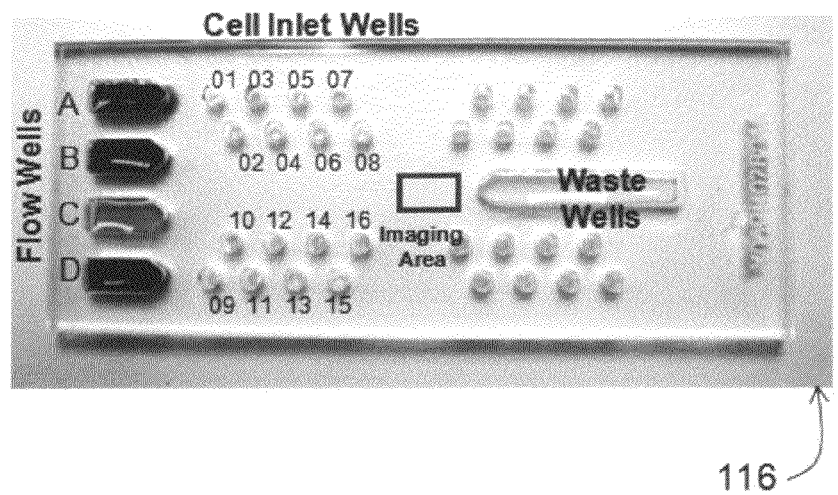
FIG. 9 shows an embodiment of the device for yeast cell imaging.

FIG. 9 shows an image of an actual fabricated embodiment of the device for yeast cell imaging. The device is similar to that shown in the schematic in FIG. 7. This particular embodiment of the device is 24 mm in width and 60 mm in length, with microchannels of 30 µm in height, and two trapping regions having internal dimensions of 8 μm and 3 μm, respectively. In this example, there are 16 yeast cell trapping regions arrayed along a common flow channel.

Figures 10A, 10B:
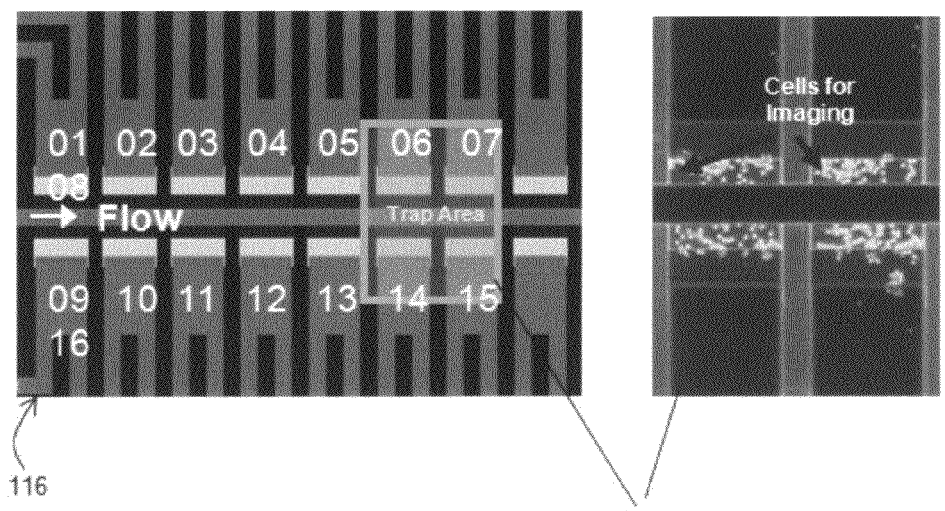
FIG. 10A shows an embodiment of the device for yeast cell imaging.
FIG. 10B shown a picture of yeast cells trapped inside the channels the device shown in FIG. 10A.

FIG. 10A shows a detailed view of the imaging area indicated in FIG. 9. The imaging area includes the trapping regions with deformable wall portions. FIG. 10B shows an image of yeast trapped in the trap area indicated in FIG. 10A. Up to 4 trapping regions are visible under a single field of a 20× objective microscope lens. Yeast cells for use with this embodiment have an average size of 5 μm; therefore, the yeast cells are trapped only in the 3 μm trapping region. The device is capable of trapping yeast from up to 16 different particle preparations (for example, 16 yeast strains, each with a different genetic modification), and introducing up to 4 different reagents, e.g., for yeast gene expression study.

D. Microfluidic Bead-Based Immunoassay

Figure 11:
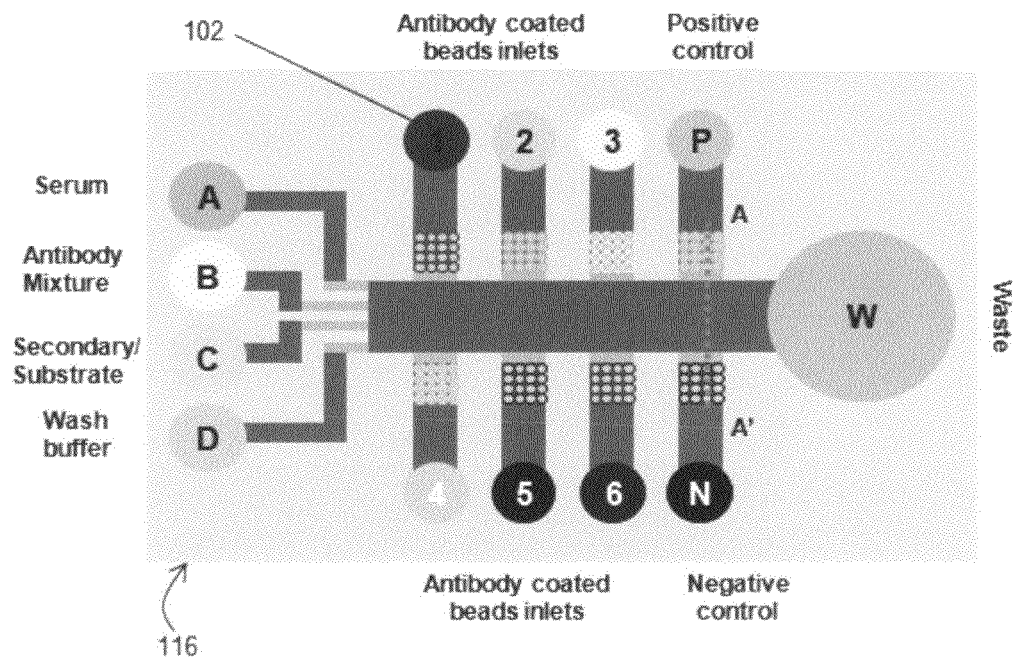
FIG. 11 shows a schematic of an embodiment of the device for trapping beads as used for immunoassays.

In related embodiments, the microfluidic particle trapping body 116 is adapted for "lab-on-a-chip" diagnosis. FIG. 11 shows a schematic design of a microfluidic bead-based immunoassay chip embodiment of the device. The exemplary assay uses the "sandwich" immunoassay method. Different biomarkers (e.g., antibodies for different disease-associated antigens) can be immobilized on beads and introduced into the trapping regions 112, which are similar to those depicted in FIGS. 10A and 10B. A microfluidic mesh region 206, or an additional trapping layer having an insufficient height to allow the passage of the particles 204, may optionally be used to prevent the beads from one trapping region from crossing into other trapping regions.

Figure 12:
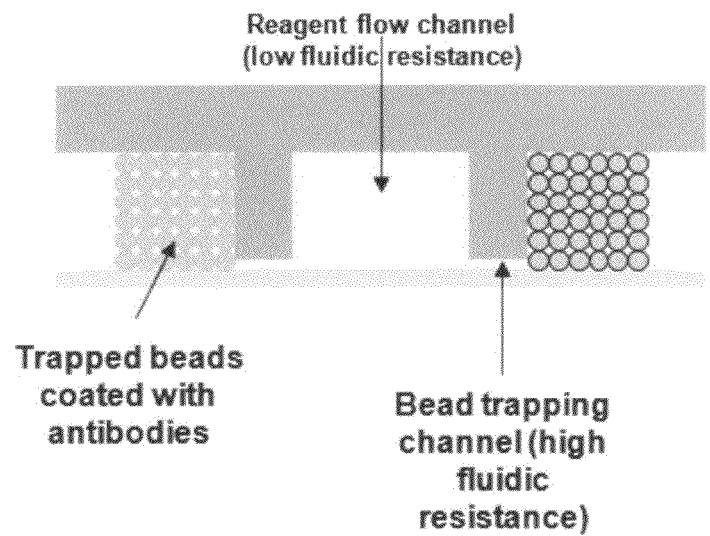
FIG. 12 shows a cross-section of an embodiment of the device. The antibody-coated beads are concentrated inside the trapping region, and are subjected to a conventional assay protocol through reagent switching.
Figures 13A, 13B, 13C:
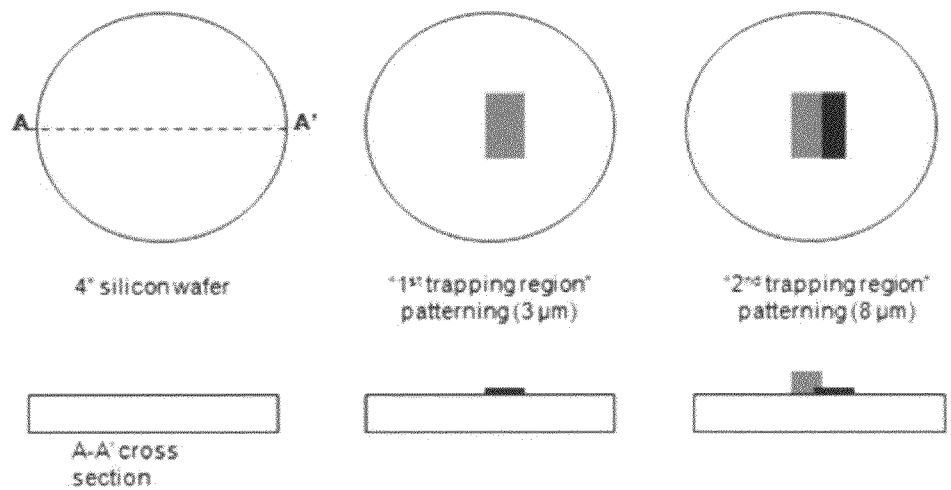
FIGS. 13A-13K illustrate steps in an exemplary fabrication method for making a microfluidic particle analysis device.
Figures 13D, 13E, 13F:
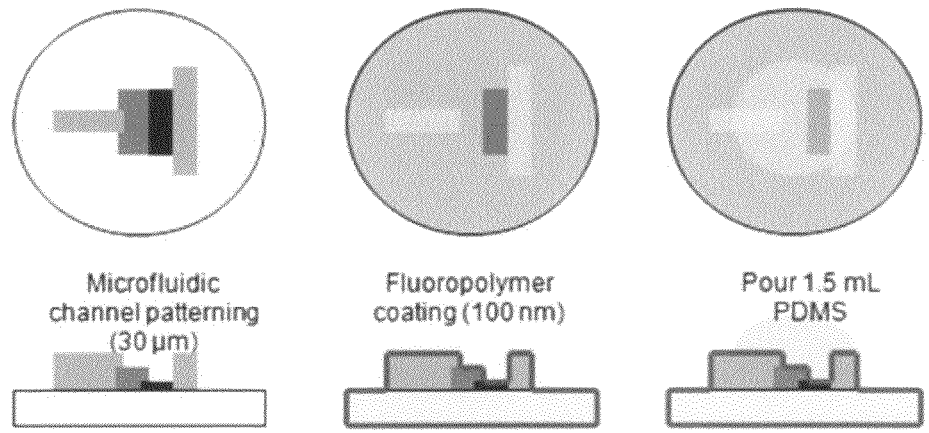
Figure 13G:
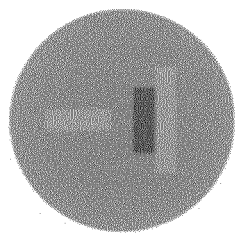
Figure 13G:
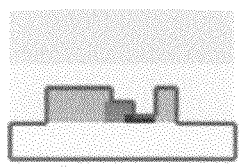
Figure 13H:
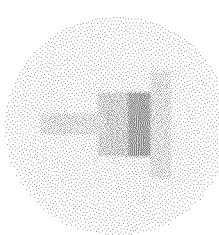
Figure 13I:
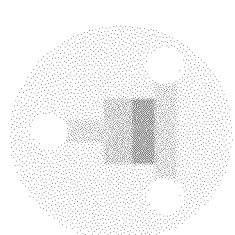
Figure 13J:
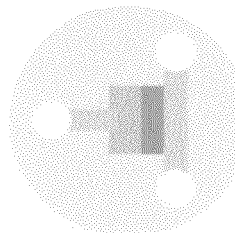
Figure 13J:
Figure 13K:
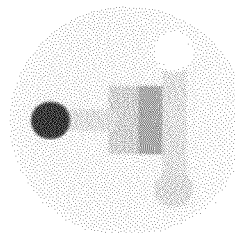
Figure 13K:
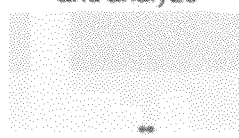

After the beads are trapped (as shown in FIG. 12), a solution or suspension, such as a patient's serum, is introduced into the trapping regions 112 from an inlet port 104 at a pressure insufficient to raise the height of the trapping region, thereby exposing the trapped beads coated with different antibodies to the serum without releasing the beads from the trapping region. Matching antigens present in the serum bind to the antibody coated beads. After washing out the serum (e.g., with a saline solution, such as PBS), an antibody mixture with specificity to the desired antigens is introduced to label the bound antigens. A secondary antibody and fluorescent substrate is typically then introduced, and the calorimetric, fluorescent, radioactive, or other signal can be analyzed using standard detection methods, where the signal from each microchamber is correlated to a specific antigen, such as a biomarker.

A key feature of this immunoassay that distinguishes it from other chip-based diagnostic assays is that the trapping region acts like a "concentrator" by packing the beads into a single layer. In this manner, particles present in three-dimensional space (i.e., in a fluid volume) are concentrated into essentially two-dimensions, because the third dimension is approximately the same height as the trapped particles. Concentrating the particles greatly increased the signal-to-noise ratio compared to conventional assays.

E. Microfabrication Methods

FIGS. 13A-13K show an exemplary method for manufacturing a microfluidic particle trapping device. The various steps are labeled A-K. The process starts with a blank, 4" test-grade silicon wafer (A). A negative photoresist (SU8 2002 Microchem) is spin coated at a final thickness of 3 μm and the first trapping region is patterned through standard photolithography (B). A second layer of negative photoresist (SU8 2005 Microchem) is spin coated at a final thickness of 8 μm and the second trapping region is patterned through standard photolithography (C). A third layer of negative photoresist (SU8 2025 Microchem) is spin coated at a final thickness of 30 μm and the rest of the microfluidic structures are patterned through standard photolithography (D). The mold is then coated with a 100 nm thick fluoropolymer using $C_4F_8$ plasma (1 torr, 300 W, 3 minutes, Surface Technology System) to create an extremely hydrophobic surface (contact angle ~140° C.) to increase mold durability and prevent PDMS stiction (E).

The molding process starts with pouring 1.5 mL PDMS (Sylgard 184, Dow Corning, 10-parts monomer mixed with 1-part curing agent) on the 4" fluoropolymer-coated silicon mold (F). The PDMS is degassed in a vacuum chamber (26" Hg for 30 minutes to remove bubbles generated during the mixing). A 3 mm thick PMMA sheet is spin coated with a primer (Sylgard PrimeCoat, Dow Corning) and pressed onto the mold (G). The mold is placed in a 60° C. oven for 2 hours to allow the PDMS to cure. After removing the mold from the oven, the PMMA sheet is detached from the silicon mold (H). Because the surface of the PMMA sheet is modified by the primer, the cured PDMS adheres to the PMMA sheet and is detached from the silicon mold with the PMMA sheet. Fluidic reservoirs are cut by a $CO_2$ laser writer (VersaLaser, 25 W) (I). The laser writer is equipped with precise step motors; therefore, the reservoirs can be cut at specific locations with high accuracy. The mold replicate is then bonded to a #1 coverglass (J) after oxygen plasma treatment (200 mtorr, 10 W, 15 seconds, TechnicsLab) to render the PDMS surface hydroxyl group rich. The device is then primed with distilled deionized water and sealed with gas impermeable tape to avoid evaporation before use (K).

Figure 14C:
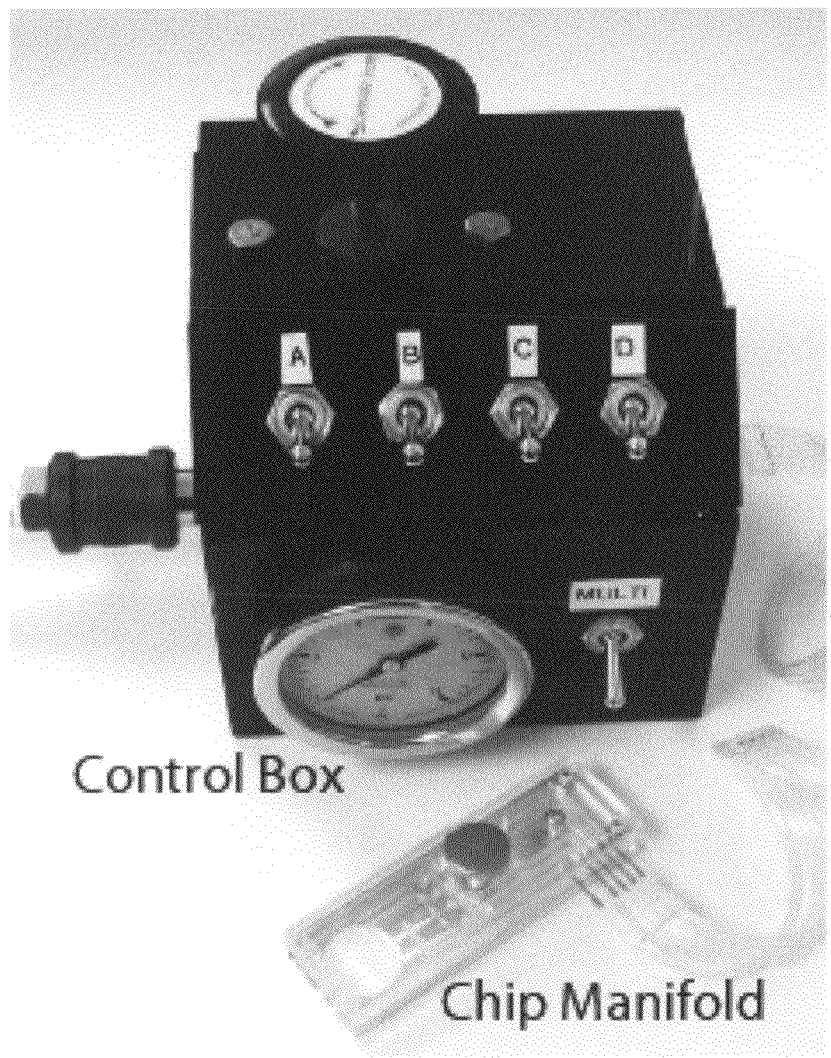

Exemplary embodiments of the device are shown in FIGS. 14A and 14B. The device may be connected to a manifold of a control box (or pressure regulator) for applying pneumatic pressure, such as the unit shown in FIG. 14. The device slides into the manifold, where a silicone gasket with openings aligns with the reservoirs of the device. The center (seal/release) knob is hand tightened so the silicone gasket and the device form a seal. An imaging window is cut from the bottom of the manifold to enable microscopy. The control box can be connected to a laboratory air pressure line, air compressor pump, or other suitable source of air pressure. The control box is equipped with a precision pressure regulator (0 to 5 psi) to control the flow rate and the amount of deformation of the trapping regions.

The above description and illustrations are provided only to exemplify the methods and the device for particle analysis. Addition aspects and embodiments will be apparent to the skilled artisan without departing from the scope of the invention.

It is claimed:
1. A microfluidic particle analysis device comprising:
   a microfluidics body;
   a microfluidics channel in said body holding a fluid flow of a liquid containing one or more cell-sized particles, said fluid flow provided via a port in communication with said microfluidics channel, said port providing two different operational pressures of said fluid flow;
   at least one trapping region of said microfluidics channel, said at least one trapping region comprising a deformable wall portion configured to have two operational heights when subjected to the two different operational pressures applied by said fluid flow in said channel, the two operational heights of the deformable wall portion comprising:

a first height configured to allow one or more cell-sized particles of interest to pass into said trapping region via said fluid flow in said channel; and a second height configured to trap one or more cell-sized particles of a given size within said trapping region of said channel by contacting said one or more cell-sized particles to substantially prevent movement of said one or more cell-sized particles, and to allow fluid flow through said trapping region via said fluid flow in said channel;

such that said one or more cell-sized particles having a given size are selectively retained in said trapping region by a change in physical dimensions of said region caused by a change in pressure applied in the channel containing the particles;

wherein said two different operating pressures are pressures applied in the microfluidics channel by the liquid carrying the particles and that do not damage cells in said channel and do not appreciably deform portions of said channel outside of said trapping region.

2. The device of claim 1, wherein said second height of said deformable wall portion comprises a relaxed condition, at which particles of a selected size are prevented from entering the trapping region, and said first height of said deformable wall portion comprises an expanded position at which particles of a selected size may enter and flow through the trapping region, wherein the expanded position is caused by pressure in the channel from at least one of said two different operational pressures.

3. The device of claim 2, wherein said trapping region further comprises a cavity in said deformable wall portion, wherein movement of the deformable wall portion from the relaxed condition to the expanded position allows particles of a selected size to enter and flow through said cavity, and movement of said deformable wall portion from the expanded position to the relaxed condition allows such particles to be trapped within said cavity in said trapping region.

4. The device of claim 1, additionally comprising a microfluidic mesh in fluid contact with the microfluidic channel, wherein the mesh prevents the passage of particles from the micro fluidic channel to a channel outlet downstream of the particle capture region.

5. The device of claim 1, wherein the microfluidic passageway has a plurality of longitudinally spaced capture regions, each defined by a deformable wall portion, each trapping region configured to trap particles of different diameters.

6. The device of claim 1, wherein the deformable wall portion is formed of a deformable polymer selected from the group consisting of polydimethylsiloxane (PDMS), polyisoprene, polybutadiene, polychloroprene, polyisobutylene, poly(styrene-butadiene-styrene), polyurethane, and silicone.

7. The device of claim 1, containing an array of such channels and associated deformable wall portions.

8. The device of claim 1, further comprising a solution inlet port in communication with said microfluidics channel, wherein the selectively retained particles are addressed with a solution from said solution inlet port.

9. The device of claim 8, wherein the selectively retained particles are addressed with a plurality of solutions in series from said solution inlet port.

10. The device of claim 8, wherein the solution comprises a drug, a reagent, a nutrient, blood, or serum.

11. The device of claim 1, wherein said two different operational pressures of said fluid flow are provided via pneumatic pressure delivered to said port.

12. The device of claim 1, wherein at least one of said two different operational pressures comprises vacuum.

13. The device of claim 12, wherein said deformable wall portion is actuated to the first operational height in response to said vacuum.

14. The device of claim 1, wherein at least one of said two different operational pressures comprises the pressure external to the device.

15. The device of claim 14, wherein said deformable wall portion is actuated to the second operational height in response to said pressure external to the device.

16. The device of claim 1, wherein the deformable wall portion is biased towards the second operational height.

17. The device of claim 1, wherein the selectively retained particles are addressed with a solution from said port.

18. The device of claim 1, further comprising a manifold in communication with the port for delivering pneumatic pressure.

19. The device of claim 18, wherein the manifold comprises an imaging window for viewing cell-sized particles within the trapping region.

20. The device of claim 1, wherein the deformable wall portion comprises a third operational height, the third operational height configured to prevent one or more cell-sized particles of interest to pass through said trapping region.

* * * * *